United States Patent
Ozawa et al.

(10) Patent No.: US 6,187,857 B1
(45) Date of Patent: Feb. 13, 2001

(54) DIPPING LATEX COMPOSITION AND RUBBER ARTICLES MADE THEREFROM BY DIPPING

(75) Inventors: Yutaka Ozawa, Tokyo; Hisanori Ohta, Kawasaki, both of (JP)

(73) Assignee: Nippon Zeon Co., Ltd., Tokyo (JP)

(*) Notice: Under 35 U.S.C. 154(b), the term of this patent shall be extended for 0 days.

(21) Appl. No.: 09/230,257

(22) PCT Filed: Jul. 23, 1997

(86) PCT No.: PCT/JP97/02547

§ 371 Date: Jan. 22, 1999

§ 102(e) Date: Jan. 22, 1999

(87) PCT Pub. No.: WO98/03584

PCT Pub. Date: Jan. 29, 1998

(30) Foreign Application Priority Data

Jul. 23, 1996 (JP) .................................................. 8-210493

(51) Int. Cl.⁷ ...................................................... C08F 8/34
(52) U.S. Cl. ........................ 524/565; 524/566; 525/329.3; 525/332.7; 525/352
(58) Field of Search .................... 524/565, 566; 525/329.3, 332.7, 352

(56) References Cited

U.S. PATENT DOCUMENTS

| | | | |
|---|---|---|---|
| 4,094,863 | * 6/1978 | Brooks et al. | 524/566 |
| 4,133,799 | * 1/1979 | Layer | 528/245 |
| 4,298,522 | * 11/1981 | Tamura et al. | 526/288 |
| 5,084,514 | * 1/1992 | Szezechura et al. | 525/123 |
| 6,031,042 | * 2/2000 | Lipinski | 524/566 |

FOREIGN PATENT DOCUMENTS

| | | |
|---|---|---|
| 2-111373 | 4/1990 | (JP) . |
| 4-333604 | 11/1992 | (JP) . |
| 5-76589 | 3/1993 | (JP) . |
| 6-299000 | 10/1994 | (JP) . |
| 8-81503 | 3/1996 | (JP) . |

* cited by examiner

Primary Examiner—Bernard Lipman
(74) Attorney, Agent, or Firm—Birch, Stewart, Kolasch & Birch, LLP

(57) ABSTRACT

A vulcanizable dip-forming rubber latex composition comprising an unsaturated nitrile-conjugated diene copolymer rubber latex, a sulfur-containing vulcanizer, and a vulcanization accelerator comprising at least one compound selected from (i) dithiocarbamic acid compounds of the formula:

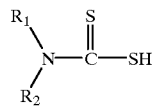

(1)

and (ii) zinc dithiocarbamate compounds of the formula:

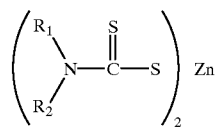

(2)

wherein $R_1$ and $R_2$ are hydrocarbon groups having at least 6 carbon atoms which may be the same or different, and an optional thiazole compound. A rubber article dip-formed from the rubber latex composition has no crack occurrence, good surface luster and good vulcanization properties, and does not contain a nitrosamine, and therefore, is suitable for medical use.

14 Claims, No Drawings

DIPPING LATEX COMPOSITION AND RUBBER ARTICLES MADE THEREFROM BY DIPPING

This application is the national phase under 35 U.S.C. §371 of prior PCT International Application No. PCT/JP97/02547 which has an International filing date of Jul. 23, 1997 which designated the United States of America.

TECHNICAL FIELD

This invention relates to a dip-forming, vulcanizable rubber latex composition comprising a sulfur-containing vulcanizer an a vulcanization accelerator, which is used for making a vulcanized unsaturated nitrile rubber article without production of a nitrosamine which is restricted by regulation, and further relates to a rubber article dip-formed therefrom.

BACKGROUND ART

Certain N-nitrosamines (hereinafter abbreviated to "nitrosamines") are carcinogenic, and a problem arises in that it is possible that nitrosamines are produced in vulcanized rubber articles made from a solid polymer rubber or a polymer rubber latex.

For example, as examples of the vulcanized rubber articles made from a polymer rubber latex, there can be mentioned those which are used in contact with the human body, such as a nipple, a balloon, gloves for operation, or medical examination or detection, a balloon sac, and other medical articles. It is possible that nitrosamines are detected in these vulcanized rubber articles. Especially a serious problem is caused in medical rubber articles which are used in direct contact with mucous membranes or organs.

At present, the restriction of nitrosamines contained in vulcanized rubber articles by regulation is an urgent problem in Japan and many other countries. Already in German, the maximum permissible amount of specific nitrosamines is 10 ppb or below. As such nitrosamines which are restricted by regulation, there can be mentioned seven species, which include, for example, N-nitrosodimethylamine, N-nitrosodiethylamine, N-nitrosodi-n-butylamine and N-nitrosomethylphenylamine.

It is known that the occurrence of nitrosamines in vulcanized rubber articles is due to the fact that a dithiocarbamic acid compound used as a polymerization terminator for emulsion polymerization or as a vulcanization promoter emulsifier remains in a solid polymer rubber or polymer rubber latex. Namely, the dithiocarbamic acid compound is hydrolyzed to produce a secondary amine which in turn reacts with $NO_x$ in the environment or nitrites or other $NO_x$ contained in food or the saliva to produce nitrosamines.

Thus it has been studied to use dithiocarbamic acid compounds as a vulcanization accelerator for rubber, which produce only a negligible amount of a nitrosamine or a secondary amine, i.e., a precursor of nitrosamine. As an example of such dithiocarbamic acid compounds, there can be mentioned zinc dibenzyldithiocarbamate. However, it is reported that when this vulcanization accelerator is used for a natural rubber latex, the resulting vulcanized rubbers generally have poor vulcanization properties as compared with vulcanized rubbers made with other conventional vulcanization accelerators (Polymer Digest, 1987, 12, p12–). The present inventors have also confirmed that when zinc dithiocarbamates are incorporated in a natural rubber latex, rubber articles dip-formed from the natural rubber latex have cracks and poor surface luster.

A vulcanization accelerator incapable of producing a nitrosamine, which is different from the dithiocarbamic acid compound vulcanization accelerator, such as zinc isopropylxanthogenate, has also been reported. This vulcanization accelerator is however little or no practicality because it has a low storage stability and an offensive smell, and results in rubber vulcanizates with poor vulcanization properties.

Other types of vulcanization accelerators such as thiophosphate compounds, thiazole compounds, benzothiazole-sulphenamide compounds and guanidine compounds are known, but desired vulcanization properties cannot be obtained with these vulcanization accelerators (Polymer Digest, 1991, 1, p65–).

Thus there is an increasing demand for a vulcanization accelerator which is incapable of producing a nitrosamine or a secondary amine and giving a vulcanized rubber having good vulcanization properties.

DISCLOSURE OF INVENTION

To solve the problems encountered with the conventional vulcanization promoters, the present inventors have conducted researches into vulcanization accelerators and found that, when specified dithiocarbamic acid compounds are used as a vulcanization accelerator for an unsaturated nitrile rubber (NBR) latex, a vulcanized rubber article dip-formed therefrom has no crack occurrence, excellent surface luster and good vulcanization properties. Based on this finding, the present invention has been completed.

Thus in accordance with the present invention there is provided a vulcanizable dip-forming rubber latex composition characterized as comprising an unsaturated nitrile-conjugated diene copolymer rubber latex, a sulfur-containing vulcanizer, at least one vulcanization accelerator selected from (i) dithiocarbamic acid compounds represented by the formula (1):

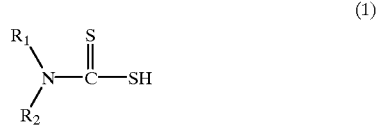

wherein $R_1$ and $R_2$ are hydrocarbon groups having at least 6 carbon atoms which may be the same as or different from each other, and (ii) zinc dithiocarbamate compounds represented by the formula (2):

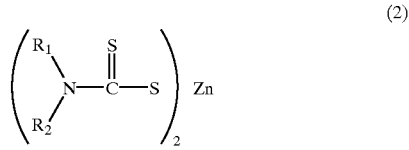

wherein $R_1$ and $R_2$ are hydrocarbon groups having at least 6 carbon atoms which may be the same as or different from each other, and an optional thiazole compound vulcanization accelerator.

Further, in accordance with the present invention, there is provided a rubber article dip-formed from the above-mentioned vulcanizable dip-forming rubber latex composition.

BEST MODE FOR CARRYING OUT THE INVENTION

The embodiments of the present invention will now be described in detail.

The main point of the present invention lies, for the production of a vulcanized rubber article by dip-forming a sulfur-vulcanizable polymer rubber latex, in the use of an unsaturated nitrile-conjugated diene copolymer rubber as the polymer rubber, and a sulfur-containing vulcanizer and, in combination therewith, a dithiocabamic acid compound of the formula (1) and/or a zinc dithiocarbamate compound of the formula (2) as the vulcanization accelerator.

Vulcanizable Dip-forming Rubber Latex Composition

The unsaturated nitrile-conjugated diene copolymer rubber latex used in the dip-forming rubber latex composition is a latex of a copolymer rubber prepared by copolymerizing a conjugated diene monomer, an ethylenically unsaturated nitrile monomer, and optional copolymerizable ethylenically unsaturated acid monomer and/or other ethylenically unsaturated monomer.

The conjugated diene monomer used for the preparation of the unsaturated nitrile-conjugated diene copolymer rubber is not particularly limited and Includes, for example, 1,3-butadiene, isoprene, 2,3-dimethyl-1,3-butadiene, 2-ethyl-1,3-butadiene. 1,3-pentadiene and chloroprene. Especially 1,3-butadiene and isoprene are preferable. These conjugated diene monomers may be used either alone or as a combination of at least two thereof. The amount of the conjugated diene monomer is usually in the range of 30 to 90% by weight and preferably 35 to 80% by weight, based on the total weight of the monomers. If the amount of the conjugated diene monomer is smaller than 30% by weight, the vulcanized rubber article dip-formed from the latex composition has rigid feeling. In contrast, if the amount thereof is larger than 90% by weight, the vulcanized rubber article dip-formed from the latex has a poor oil resistance and low tensile strength and tear strength.

The ethylenically unsaturated nitrile monomer is not particularly limited and includes, for example, acrylonitrile, methacrylonitrile, fumaronitrile, α-chloroacrylonitrile and α-cyanoethylacrylonitrile. These ethylenically unsaturated nitrile monomers may be used either alone or as a combination of at least two thereof. The amount of the ethylenically unsaturated nitrile monomers is usually in the range of 9 to 50% by weight and preferably 20 to 45% by weight, based on the total weight of the monomers. If the amount of the unsaturated nitrile monomer is smaller than 9% by weight, the vulcanized rubber article dip-formed from the latex composition has a poor oil resistance. In contrast, if the amount thereof is larger than 50% by weight, the vulcanized rubber article dip-formed from the latex has a rigid feeling.

The ethylenically unsaturated acid monomer optionally used includes ethylenically unsaturated monomers having an acid group such as a carboxyl group, a sulfonic acid group and an acid anhydride group. As specific examples thereof, there can be mentioned ethylenically unsaturated carboxylic acids such as acrylic acid, methacrylic acid, itaconic acid maleic acid and fumaric acid; polycarboxylic acid anhydrides such as maleic anhydride and citraconic anhydride; ethylenically unsaturated sulfonic acid monomers such as styreneslulfonic acid; and partial ester monomers of an ethylenically unsaturated polycarboxylic acid such as monobutyl fumarate, monobutyl maleate and mono-2-hydroxypropyl maleate. These ethylenically unsaturated polycarboxylic acid monomers may also be used as an alkali metal salt or an ammonium salt. These ethylenically unsaturated acid monomers may be used either alone or as a combination of at least two thereof. The amount of the ethylenically unsaturated acid monomers is usually not larger than 20% by weight, preferably in the range of 1 to 15% by weight and more preferably 2 to 10% by weight, based on the total weight of the monomers. If the amount of the acid monomer is larger than 20% by weight, the vulcanized rubber article dip-formed therefrom has a poor tear strength and a rigid feeling.

As specific examples of the other copolymerizable ethylenically unsaturated monomer optionally used for copolymerization, there can be mentioned vinyl aromatic monomers such as styrene, alkylstyrenes and vinylnaphthalenes; fluoroalkyl vinyl ethers such as fluoroethyl vinyl ether; ethylenically unsaturated amide monomers such as acrylamide, methacrylamide, N-methylolacrylamide, N-methylolmethacryl-amide, N,N-dimethylolacrylamide, N,N-dimethylolmethacryl-amide, N-methoxymethylacrylamide, N-methoxymethylmethacryl-amide, N-propoxymethylacrylamide and N-propoxymethylmethacrylamide; vinylpyridine; vinylnorbornene; non-conjugated diene monomers such as dicyclopentadiene and 1,4-hexadiene; and ethylenically unsaturated carboxylic acid esters such as methyl acrylate, methyl methacrylate, ethyl acrylate, ethyl methacrylate, butyl acrylate, butyl methacrylate, 2-ethylhexyl acrylate, 2-ethylhexyl methacrylate, trifluoroethyl acrylate, trifluoroethyl methacrylate, tetrafluoropropyl acrylate, tetrafluoropropyl methacrylate, dibutyl maleate, dibutyl fumarate, diethyl maleate, methoxymethyl acrylate, methoxymethyl methacrylate, ethoxy-ethyl acrylate, ethoxyethyl methacrylate, methoxyethoxyethyl acrylate, methoxyethoxyethyl methacrylate, cyanomethyl acrylate, cyanomethyl methacrylate, 2-cyanoethyl acrylate, 2-cyanoethyl methacrylate, 1-cyanopropyl acrylate, 1-cyano-propyl methacrylate, 2-ethyl-6-cyanohexyl acrylate, 2-ethyl-6-cyanohexyl methacrylate, 3-cyanopropyl acrylate, 3-cyanopropyl methacrylate, hydroxyethyl acrylate, hydroxyethyl methacrylate, hydroxypropyl acrylate, hydroxypropyl methacrylate, glycidyl acrylate, glycidyl methacrylate, dimethylaminoethyl acrylate and diemthylaminoethyl methacrylate. These ethylenically unsaturated monomers may be used either alone or as a combination of at least two thereof. The amount of these ethylenically unsaturated monomers is usually not larger than 20% by weight based on the total weight of the monomers.

The molecular weight of the unsaturated nitrile-conjugated diene copolymer Is not particularly limited, but is usually in the range of 50,000 to 500,000 and preferably 80,000 to 200,000 as a weight average molecular weight expressed in terms of that of standard polystyrene (hereinafter merely referred to as molecular weight). If the molecular weight is too small, a rubber article dip-formed therefrom has a low tensile strength. In contrast, if the molecular weight is too large, a rubber article dip-formed therefrom has a rigid feeling.

The unsaturated nitrile-conjugated diene copolymer rubber latex is prepared usually by an emulsion polymerization procedure. The temperature at which the emulsion polymerization is effected is not particularly limited, but is preferably not higher than about 40° C. because the latex can be produced stably and a rubber article dip-formed therefrom has a high mechanical strength and a soft feeling.

The manner in which the monomers are added is not particularly limited. Any manner can be employed in which the monomer mixture is charged into a polymerization reactor at once or continuously, or part of the monomer mixture is charged in a polymerization reactor and the remainder is continuously introduced therein.

A polymerization initiator used is not particularly limited, but a redox polymerization initiator is preferable. Preferable peroxides used in the redox initiator are those which have a half-life of 10 hours at a temperature of at least 100° C., and, specific examples of the peroxides, there can be mentioned hydroperoxides such as diisopropylbenzone hydroperoxide, cumene hydroperoxide, t-butyl hydroperoxide, 1,1,3,3-tetramethylbutyl hydroperoxide and 2,5-dimethylhexane-2, 5-dihydroperoxide. Especially those which have a half-life of 10 hours at a temperature of at least 130° C., such as, for example, 1,1,3,3-tetramethylbutyl hydroperoxide, are preferable because the rubber latex can be stably produced and a rubber article dip-formed therefrom has a high mechanical strength and a soft feeling. The amount of the peroxide varies to some extent depending upon the particular peroxide, but is preferably in the range of 0.01 to 0.6% by weight based on the monomer mixture.

The reducing agent component used in the redox polymerization initiator is not particularly limited, and includes, for example, compounds containing a metal ion in a reduced state such as ferrous sulfate and cuprous naphthenate; sulfonic acid compounds such as sodium methanesulfonate; and amine compounds such as dimethylaniline. These reducing agents may be used either alone or as a combination of at least two thereof. The amount of the reducing agent varies to some extent depending upon the particular reducing agent, but is preferably in the range of 0.03 to 10 parts by weight based on 1 part by weight of the peroxide.

An emulsifier used for the preparation of the unsaturated nitrile-conjugated diene copolymer rubber is not particularly limited. As specific examples of the emulsifier, there can be mentioned nonionic emulsifiers such as polyoxyethylene alkylether, polyoxyethylene alkylphenolether, polyoxyethylene alkylester and polyoxyethylenesorbitan alkylester; anionic emulsifiers such as fatty acids, for example, myristic acid, palmitic acid, oleic acid and linolenic acid, and their salts, higher alcohol sulfate esters and alkylsulfosuccinic acids; cationic emulsifiers such as ammonium chlorides, for example, trimethylammonium chloride and dialkylammonium chlorides, benzylammonium salts and quaternary ammonium salts; and copolymerizable emulsifiers such as sulfoesters of α, β-unsaturated carboxylic acids, sulfate esters of α, β-unsaturated carboxylic acids and sulfoalkylarylethers of α, β-unsaturated carboxylic acids. Of these, anionic emulsifiers and nonionic emulsifiers are preferable. These emulsifiers may be used either alone or as a combination of at least two thereof. The amount of the emulsifier is not particularly limited, but is preferably in the range of 0.1 to 9.0% by weight based on the monomer mixture.

In the course of polymerization, when the predetermined conversion is reached, a polymerization terminator is added into the polymerization system to stop polymerization. The polymerization terminator used is not particularly limited and conventional terminators having an amine structure such as hydroxylamine and sodium dimethyldithiocarbamate can be used. However, it Is preferable to use a polymerization terminator which does not give an offensive smell and is incapable of producing a nitrosamine or capable of producing only a very minor amount of a nitrosamine, which is restricted by regulation. As specific examples of such polymerization terminators, there can be mentioned diethylhydroxylamine, hydroxylaminesulfonic acid and its alkali metal salts, hydroxylaminesulfate salts, aromatic hydroxydithiocarboxylic acids such as hydroxyl-dimethylbenezenethiocarboxylic acid, hydroxyldiethyl-benezenethiocarboxylic acid and hydroxyldibutylbenezene-thiocarboxylic acid, and their alkali metal salts, hydroquinone derivatives and catechol derivatives.

These radical polymerization terminators may be used either alone or as a combination of at least two thereof. The amount of the polymerization terminator is not particularly limited but is usually in the range of 0.1 to 10 parts by weight based on 100 parts by weight of the total monomers.

By using the polymerization terminator incapable of producing a nitrosamine or capable of producing only a very minor amount of a nitrosamine, which gives an offensive smell, in combination with the specified vulcanization accelerator, the content of the nitrosamines in a rubber article dip-formed therefrom can be controlled to zero or an negligible extent. The amount of the nitrosamines extracted from the rubber article dip-formed therefrom (said amount can be measured by the method mentioned hereinafter) is generally not larger than 1 ppm. By more suitably choosing the polymerization terminator and the vulcanization accelerator, the amount of the nitrosamines extracted can be lowered to a level of not larger than 0.1 ppm.

When the unsaturated nitrile-conjugated diene copolymer rubber latex is prepared, a molecular weight modifier, a particle diameter adjuster, an anti-aging agent, a chelating agent, an oxygen-capturing agent and other polymerization auxiliaries can be used according to the need.

The sulfur-containing vulcanizer used in the present invention includes sulfur and sulfur-containing compounds which are generally used as a sulfur-containing vulcanizer for polymer rubber latexes. As specific examples of the sulfur-containing vulcanizer, there can be mentioned sulfur such as powdery sulfur, flower of sulfur, precipitated sulfur, colloidal sulfur, surface-treated sulfur and insoluble sulfur; and sulfur-containing compounds such as sulfur chloride, sulfur dichloride, morpholine disulfide, an alkylphenol disulfide, N,N'-dithio-bis(hexahydro-2H-azepinone-2), phosphorus-containing polysulfide, high-molecular-weight polysulfide, tetramethyl-thiuram disulfide, selenium dimethyldithiocarbamate and 2-(4'-morpholinodithio)benzothiazole.

The amount of the sulfur-containing vulcanizer is not particularly limited, but Is usually in the range of 0.10 to 10 parts by weight and preferably 0.1 to 5 parts by weight, based on 100 parts by weight of the unsaturated nitrile-conjugated diene copolymer rubber.

In the present invention, in combination with the sulfur-containing vulcanizer, a vulcanization accelerator selected from (i) dithiocarbamic acid compounds represented by the formula (1) and/or (ii) zinc dithiocarbamate compounds represented by the formula (2) is used optionally with a thiazole vulcanization accelerator.

In the formulae (1) and (2), $R_1$ and $R_2$ are hydrocarbon groups having at least 6 carbon atoms which may be the same as or different from each other. As examples of $R_1$ and $R_2$, there can be mentioned an alkyl or cycloalkyl group which may have a branch, an aryl group which may have a substituent, and a benzyl group which may have one or two alkyl groups each having 1 to 5 carbon atoms in the α-carbon atom.

As specific examples of the dithiocarbamic acid compounds of the formula (1), there can be mentioned dibenzyldithio-carbamic acid, di-2-ethylhexyldithiocarbamic acid, diphenyldithiocarbamic acid and dicyclohexyldithiocarbamic acid. As specific examples of the zinc dithiocarbamate compounds of the formula (2), there can be mentioned zinc salts of the above-recited dithiocarbamic acid compounds. Dibenzyldithiocarbamic acid and its zinc salt are especially preferable. These compounds have an excellent dispersibility in water and rubber articles dip-formed therefrom have no color.

The dithiocarbamic acid vulcanization accelerators used in the present invention do not produce a nitrosamine which is restricted by regulation. The dithiocarbamic acid vulcanization accelerators can exhibit a vulcanization accelerating activity and can impart vulcanization properties to rubber articles dip-formed therefrom, which are similar to those given by the conventional dithiocarbamic acid vulcanization accelerators which are considered in the art to be indispensable for making rubber articles by dip-forming and which produce nitrosamines restricted by regulation. The rubber articles dip-formed from the latex composition with the vulcanization accelerator used in the present invention do not give an offensive smell, are not colored or are colored only to a negligible extent, do not have cracks or have very few cracks, and have an excellent surface luster.

Even if the above-mentioned dithiocarbamic acid and/or zinc dithiocarbamate vulcanization accelerator is used alone, vulcanization properties of the desired extent can be imparted to vulcanized rubber articles. However, when these vulcanization accelerators are used in combination with a thiazole compound vulcanization accelerator, mechanical strength and other physical properties can be varied more widely.

The thiazole compound vulcanization accelerator used includes those which have heretofore conventionally used, and, as specific examples thereof, there can be mentioned 2-mercaptobenzothiazole and its zinc salt, copper salt, sodium salt and cyclohexylamine salt; 2-mercaptothiazoline, dibenzothiazyl disulfide, 2-(2,4-dinitrophenylthio)-benzo-thiazole, 2-(N,N-diethylthiocarbaylthio)benzothiazole, 2-(2,6-dimethyl-4-morpholinothio)benzothiazole, 2-(4'-morpholinodithio) benzothiazole, 4-morpholinyl- 2-benothiazyl disulfide and 1,3-bis(2-benzothiazylmercaptomethyl)urea. Of these, 2-mercaptobenothlazole and its zinc salt, and dibenzothiazyl disulfide are preferable.

The amount of the vulcanization accelerator is suitably determined so that sufficient vulcanization can be attained and mechanical strength and other physical properties required for vulcanized rubber articles are obtained, and is not particularly limited. Usually the total amount of the vulcanization accelerator is 0.1 to 10 parts by weight based on 100 parts by weight of the solid content In the copolymer rubber latex.

When the above-mentioned two types of vulcanization accelerators are used in combination, the proportion of the two vulcanization accelerators is not particularly limited, but the ratio of the dithiocarbamic acid and/or zinc dithiocarbamate vulcanization accelerator to the thiazole compound vulcanization accelerator is preferably in the range of 9.5/0.5 to 3/7 by weight.

In addition to the above-mentioned vulcanization accelerators, zinc oxide can be used in a manner similar to the conventional sulfur vulcanization method. Active zinc oxide can be used as the zinc oxide, but is difficult to disperse. The amount of zinc oxide is suitably determined so that a sufficient vulcanization can be attained and the mechanical strength and other physical properties required for vulcanized rubber articles are obtained, and is not particularly limited.

According to the need, additives can be incorporated in the dip-forming rubber latex composition of the present invention for imparting desired properties to vulcanized rubber articles, which include, for example, reinforcers such as carbon black, silica and talc, fillers such as calcium carbonate and clay, plasticizers, anti-aging agents, and ultraviolet absorbers. Other rubber latexes such as natural rubber latex and isoprene rubber latex can be incorporated provided that the object of the present invention can be achieved.

The procedure by which the dip-forming rubber latex composition of the present invention is prepared is not particularly limited. Usually the rubber latex can be made by thoroughly mixing and dispersing together an unsaturated nitrile-conjugated diene copolymer rubber latex, a sulfur-containing vulcanizer, a vulcanization accelerator and other additives together with a dispersion stabilizer by using a conventional mixing and dispersing apparatus. The method by which the respective ingredients are added is not particularly limited, and, as a preferable method, a method can be employed wherein the copolymer rubber latex is mixed with various additives by using a dispersion stabilizer to prepare a dispersion, and the dispersion is thoroughly mixed by using a stirrer or dispersing apparatus such as a kneader or a disper.

Dip-Formed Rubber Articles

The dip-formed rubber articles of the present invention are made by dip-forming the above-mentioned vulcanizable unsaturated nitrile-conjugated diene copolymer rubber latex composition.

Usually the dip-forming is carried out by a process wherein a mold is dipped in a bath of a dip-forming rubber latex formulation whereby a rubber latex is deposited on the mold surface, the mold having the rubber latex deposit on the surface thereof is taken-up from the bath, if desired, a coating film on the mold is dried, and then is separated from the mold to obtain a rubber article. The dip-forming method includes, for example, a direct dipping method, an anode coagulant dipping method and a teague coagulant dipping method.

In the dip-forming method, a coagulant can be used, if desired, prior to dipping of the mold in a bath of a rubber latex formulation or after the dipped mold is taken-up from the bath. More specifically, for example, a mold can be pre-treated with a coagulant before the mold is dipped in the rubber latex formulation, or a solution of a coagulant can be sprayed onto a mold having a deposited rubber latex coating.

In the dip-forming method, the mold can be pre-heated before it is dipped in the rubber latex formulation or, if desired, the mold can be treated with warm water or heat-treated. By conducting the warm water-treatment or the heat-treatment, excessive monomers and additives can be removed. The specific procedure for the warm water-treatment or the heat-treatment is not particularly limited, and, as specific examples of the treatment procedure, there can be mentioned a procedure wherein the mold having a deposited rubber latex coating is dipped in a warm water bath, a procedure wherein warm air is blown against the mold having a deposited rubber latex coating in an oven, and a procedure wherein the mold having a deposited rubber latex coating is irradiated with infrared rays.

The kinds of the vulcanized rubber articles of the present invention may be the same as vulcanized rubber articles made by the conventional dip-forming methods. As specific examples of the vulcanized rubber articles, there can be mentioned gloves for operation, or medical examination or detection, medical rubber articles such as a balloon sac and a catheter balloon, a nipple, gloves for home use, gloves for industrial use, and balloons.

The invention will now be described by the following examples and comparative examples, wherein parts are by weight unless otherwise specified.

Each of the thus-made unvulcanized films was vulcanized under conditions of 100° C. for 40 minutes or 120° C. for 40 minutes in an oven to obtain a vulcanized film. The vulcanized films did not give any offensive smell and had no color.

Small modified #2 dumbbell-shaped specimens were cut from the vulcanized film, and their mechanical strength and other physical properties were evaluated. The tensile tests were conducted at a pulling speed of 500 mm/min to measure a tensile strength (kg/cm$^2$) and an elongation (%) at break. Surface luster and occurrence of cracks of the film were visually examined by naked eye. The results are shown in Table 1. Rating "A" in surface luster means that the surface luster is good, and rating "A" in crack occurrence means that crack did not occur.

TABLE 1

|  | Additives*1 | | | | Vulcanizing conditions | | | | | |
|---|---|---|---|---|---|---|---|---|---|---|
|  |  |  | | VA*2 | | 100° C. × 40 min. | | 120° C. × 40 min. | | Crack | Surface |
|  | Sulfur | Zinc oxide | A* | B* | C* | TS*3 | E1*4 | TS*3 | E1*4 | occurrence | luster |
| Comp. Exam. 1 | 2 | 2 | 0.5 | — | — | 190 | 520 | 230 | 650 | A | A |
| Example 1 | 2 | 2 | — | 0.5 | — | 215 | 520 | 245 | 630 | A | A |
| Example 2 | 2 | 2 | — | 0.5 | 0.5 | 175 | 550 | 255 | 620 | A | A |
| Example 3 | 2 | 2 | — | 1 | 1 | 285 | 560 | 310 | 600 | A | A |
| Example 4 | 1 | 3 | — | 0.5 | 0.5 | 210 | 500 | 250 | 520 | A | A |
| Example 5 | 3 | 3 | — | 0.5 | 0.5 | 120 | 700 | 120 | 740 | A | A |

Comp. Exam.: Comparative Example
*1parts/latex[solid] 100 parts
*2Vulcanization accelerator
*3Tensile strength (kg/cm$^2$)
*4Elongation (%)
A*: zinc di-n-butylthiocarbamate
B*: zinc dibenzyldithiocarbamate
C*: 2-mercaptobenzothiazole

EXAMPLES 1–5

Comparative Example 1

To an NBR (copolymer composed of acrylonitrile 27 wt. %, 1,3-butadiene 67.5 wt. % and methacrylic acid 5.5 wt. %, polymerization terminator: hydroxylamine sulfate, molecular weight: 200,000) latex, a dispersion of vulcanizer and vulcanization accelerator (kinds and amounts thereof are shown in Table 1) was added, and the mixture was thoroughly mixed and dispersed by using a stirrer to prepare a dip-forming rubber latex composition. Unvulcanized film was dip-formed from each rubber latex composition by the following coagulant dipping method.

Making a Film by Coagulant Dipping Method

A metal mold having a predetermined shape was dipped in an aqueous calcium nitrate solution having a 35 wt. % concentration for 10 seconds, and then the mold was dipped in the dip-forming rubber latex composition having a solid content of 47 wt. % for 5 seconds. The mold having a thus-deposited coating film was dried at room temperature for 30 minutes.

The content of nitrosamine in each of the films vulcanized at 140° C. for 40 minutes was measured. The results are shown in Table 2.

The measurement of the nitrosamine content was carried out as follows.

(1) The vulcanized film Is washed with a stream of warm water for 10 minutes and then dried at room temperature.

(2) 15 g of the dry film is dipped in 85 ml of methanol under stationary conditions at 90° C. for 8 hours, and then, is taken-out therefrom.

(3) The methanol containing the extracted material is concentrated at 40° C. under a reduced pressure to a volume of 5 ml.

(4) The content of nitrosamine in the methanol is measured by GS/MS-Scan. Previously calibration curves are drawn on standard materials, i.e., seven nitrosamines including N-nitrosodimethylamine, which are restricted by regulation.

TABLE 2

|  | Sulfur | ZnO | VA A | VA B | VA C | N-nitrosodi-n-butylamine(ppm) | Other nitrosamines restricted by regulations |
|---|---|---|---|---|---|---|---|
| Comp. Exam. 1 | 2 | 2 | 0.5 | — | — | 1.68 | ND |
| Example 2 | 2 | 2 | — | 0.5 | 0.5 | ND | ND |

Comp. Exam.: Comparative Example
VA: Vulcanization accelerator
ND: Not detected. Detection limit is 0.1 ppm.
A: zinc di-n-butyldithiocarbamate
B: zinc dibenzyldithiocarbamate
C: 2-mercaptobenzothiazole

EXAMPLES 6–9
Comparative Example 2

By the same procedures as employed in Example 1, vulcanized NBR films were made wherein an NBR (copolymer composed of acrylonitrile 37 wt %, 1,3-butadiene 57.5 wt. % and methacrylic acid 5.5 wt. %, polymerization terminator: hydroxylamine sulfate, molecular weight: 200,000) latex was used instead of the NBR latex used in Example 1 with all other conditions remaining the same. Mechanical properties of the films were measured and the crack occurrence and surface luster thereof were visually examined. The results are shown in Table 3.

TABLE 3

|  | Additives*1 | | | | | Vulcanizing conditions | | | |
|---|---|---|---|---|---|---|---|---|---|
|  |  |  | VA*2 | | | 100° C. × 40 min. | | 120° C. × 40 min. | |
|  | Sulfur | Zinc oxide | A* | B* | C* | TS*3 | E1*4 | TS*3 | E1*4 |
| Comp. Exam. 2 | 2 | 2 | 0.5 | — | — | 260 | 500 | 280 | 520 |
| Example 6 | 2 | 2 | — | 0.5 | — | 190 | 500 | 200 | 500 |
| Example 7 | 2 | 2 | — | 0.5 | 0.5 | 250 | 480 | 330 | 500 |
| Example 8 | 1 | 3 | — | 0.5 | 0.5 | 265 | 450 | 230 | 420 |
| Example 9 | 3 | 3 | — | 0.5 | 0.5 | 125 | 600 | 165 | 650 |

Comp. Exam.: Comparative Example
*1parts/latex[solid] 100 parts
*2Vulcanization accelerator
*3Tensile strength (kg/cm$^2$)
*4Elongation (%)
A*: zinc di-n-butyldithiocarbamate
B*: zinc dibenzyldithiocarbamate
C*: 2-mercaptobenzothiazole

EXAMPLES 10–14
Comparative Examples 3, 4

In these examples, unsupported globes were made as an example of the dip-formed rubber articles.
Preparation of Vulcanized Liquid Dispersion The following ingredients were pulverized in a ball mill for 48 hours to prepare a liquid vulcanizer dispersion having a solid content of 50 wt. %.

|  | Parts by weight |
|---|---|
| Colloidal sulfur (Hosoi Kagaku K.K.) | 2.0 |
| #1 Zinc oxide (Seido Kagaku K.K.) | 2.0 |
| Vulcanization accelerator A (see Table 1) | 0.5 |

|  | Parts by weight |
|---|---|
| Titanium oxide (JR 600A supplied by TAYCA K.K.) | 0.7 |
| Dispersant (Demol N supplied by Kao Corp.) | 0.5 |
| KOH | 0.01 |
| Water | 5.1 |

Preparation of Dip-Forming Rubber Latex Composition

The vulcanizer dispersion prepared by the above-mentioned method was added to a NBR latex according to the following recipe, and the mixture was thoroughly stirred to prepare a dip-forming rubber latex composition.

|  | Parts by weight |
|---|---|
| NBR latex* | 100 |
| Vulcanizer Dispersion | 5.71 |

*Note, latex of copolymer composed of acrylonitrile 27 wt. %, butadiene 67.5 wt. % and methacrylic acid 5.5 wt. %, (polymerization terminator: hydroxylamine sulfate, molecular weight: 200,000)

Preparation of Coagulant Solution

A coagulant solution was prepared according to the following recipe.

|  | Parts by weight |
| --- | --- |
| Calcium nitrate | 20 |
| Nonionic surface active agent (Emulgen 810 supplied by Kao Corp.) | 0.05 |
| Ethyl alcohol | 79.95 |

A ceramic mold for glove was washed and then dried at 80° C. for 20 minutes. The mold was then dipped in the coagulant solution for 1 minute, taken out from the coagulant solution, and dried at 20° C. for 30 minutes, whereby the coagulant was deposited in the mold.

Then the coagulant-deposited mold for glove was gently dipped in the dip-forming rubber latex composition over a period of 5 seconds. When 10 seconds elapsed from the immersion of the entire mold, the mold was started to take up gently from the rubber latex composition. The mold was taken up over a period of 5 seconds from the rubber latex composition, and then, dried at 20° C. for 30 minutes. The dried mold was then subjected to leaching with warm water at 40° C. for 10 minutes, dried at 80° C. for 40 minutes, and then the deposited rubber coating was vulcanized at 100° C. for 40 minutes in an oven.

After the mold was cooled, the surface of the deposited rubber coating was sprinkled with talc and then the rubber coating of a glove form was separated from the mold to obtain an unsupported NBR glove. Similarly a deposited rubber coating was vulcanized at 120° C. for 40 minutes in an oven to obtain an unsupported NBR glove. Both gloves did not give an offensive smell and had no color.

The surface luster and occurrence of cracks in the thus-made gloves were visually examined by naked eye.

Small modified #2 dumbbell-shaped specimens were cut from flat portions of the gloves, and their mechanical strength and other physical properties were evaluated. The tensile tests were conducted at a pulling speed of 500 mm/min. The results are shown in Table4. Ratings "A" and "B" in surface luster means that the surface luster is good and poor, respectively, and ratings "A" and "B" in crack occurrence means that crack did not occur and occurred, respectively.

By the same procedures as mentioned above (Example 10), unsupported gloves were made wherein the kinds and amounts of sulfur, zinc oxide and vulcanization accelerator were varied as shown in Table 4 with all other conditions remaining the same (Examples 11–14). For comparison, an unsupported natural rubber (NR) glove was made in a similar manner (Comparative Example 4). The results of evaluation of the respective gloves are shown in Table 4.

TABLE 4

|  | Additives*1 | | | | | Vulcanizing conditions | | | | Crack occurrence | Surface luster |
| --- | --- | --- | --- | --- | --- | --- | --- | --- | --- | --- | --- |
|  |  |  | VA*2 | | | 100° C. × 40 min. | | 120° C. × 40 min. | | | |
|  | Sulfur | Zinc oxide | A* | B* | C* | TS*3 | El*4 | TS*3 | El*4 | | |
| C. Ex. 3 NBR | 2 | 2 | 0.5 | — | — | 185 | 500 | 210 | 650 | A | A |
| Exam. 10 NBR | 2 | 2 | — | 0.5 | — | 205 | 550 | 255 | 610 | A | A |
| Exam. 11 NBR | 2 | 2 | — | 0.5 | 0.5 | 180 | 550 | 270 | 620 | A | A |
| Exam. 12 NBR | 2 | 2 | — | 1.0 | 1.0 | 280 | 550 | 310 | 600 | A | A |
| Exam. 13 NBR | 1 | 3 | — | 0.5 | 0.5 | 220 | 550 | 270 | 530 | A | A |
| Exam. 14 NBR | 3 | 3 | — | 0.5 | 0.5 | 135 | 680 | 160 | 730 | A | A |
| C. Ex. 4 NR | 2 | 2 | — | 0.5 | 0.5 | 150 | 800 | 170 | 850 | B | B |

C. Ex.: Comparative Example
*1parts/latex[solid] 100 parts
*2Vulcanization accelerator
*3Tensile strength (kg/cm$^2$)
*4Elongation (%)
A*: zinc di-n-butyldithiocarbamate
B*: zinc dibenzyldithiocarbamate
C*: 2-mercaptobenzothiazole Industrial Applicability Rubber articles dip-formed from the vulcanizable unsaturated nitrile-conjugated diene copolymer rubber latex composition of the present invention have no crack occurrence, excellent surface luster, and good vulcanization properties which compare with those of rubber articles made with the conventional dithiocarbamic acid compound vulcanization accelerator. The dip-formed rubber articles do not contain a nitrosamine and give no offensive smell and have no color.

Therefore, as specific examples of the dip-formed rubber articles, there can be mentioned medical rubber articles such as gloves for operation, or medical examination or detection, a balloon sac and a catheter; a nipple; gloves for home use; gloves for industrial use; and balloons.

What is claimed is:
1. A vulcanizable dip-forming rubber latex composition characterized as comprising an unsaturated nitrile-conjugated diene copolymer rubber latex, a sulfur-containing vulcanizer, at least one vulcanization accelerator selected from (i) dithiocarbamic acid compounds represented by the formula (1):

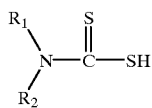
(1)

wherein $R_1$ and $R_2$ are hydrocarbon groups having at least 6 carbon atoms which may be the same as or different from each other, and (ii) zinc dithiocarbamate compounds represented by the formula (2)

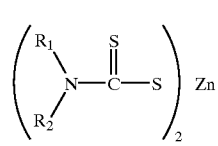
(2)

wherein $R_1$ and $R_2$ are hydrocarbon groups having at least 6 carbon atoms which may be the same as or different from each other, wherein a rubber article dip-formed from said rubber latex composition has an extracted nitrosamine content of not larger than 1 ppm.

2. The rubber latex composition according to claim 1, which comprises a thiazole compound in addition to at least one compound selected from the dithiocarbamic acid compounds of the formula (1) and the zinc dithiocarbamate compounds of the formula (2) as the vulcanization accelerator.

3. The rubber latex composition according to claim 1, which comprises 0.10 to 10 parts by weight of the sulfur-containing vulcanizer and 0.1 to 10 parts by weight of the vulcanization accelerator, based on 100 parts by weight of the unsaturated nitrile-conjugated diene copolymer rubber.

4. The rubber latex composition according to claim 2, wherein the vulcanization accelerator is a mixture comprising (A) at least one compound selected from the dithiocarbamic acid compounds of the formula (1) and the zinc dithiocarbamate compounds of the formula (2), and (B) the thiazole compound at a ratio (A:B) of 9.5:0.5 to 3:7 (weight ratio).

5. The rubber latex composition according to claim 1, wherein the unsaturated nitrile-conjugated diene copolymer rubber is a copolymer composed of 9 to 50% by weight of an ethylenically unsaturated nitrile monomer, 30 to 90% by weight of a conjugated diene monomer, 0 to 20% by weight of an ethylenically unsaturated acid monomer and 0 to 20% by weight of other ethylenically unsaturated monomer.

6. The rubber latex composition according to claim 1, wherein the unsaturated nitrile-conjugated diene copolymer rubber is a copolymer composed of 20 to 45% by weight of an ethylenically unsaturated nitrile monomer, 35 to 80% by weight of a conjugated diene monomer, 1 to 15% by weight of an ethylenically unsaturated acid monomer and 0 to 20% by weight of other ethylenically unsaturated monomer.

7. The rubber latex composition according to claim 1, wherein the unsaturated nitrile-conjugated diene copolymer rubber has a weight average molecular weight of 50,000 to 500,000 as in terms of those of standard polystyrene.

8. The rubber latex composition according to claim 1, wherein the unsaturated nitrile-conjugated diene copolymer rubber is prepared by using as a polymerization terminator at least one compound selected from diethylhydroxylamine, hydroxylaminesulfonic acid and its alkali metal salts, hydroxylamine sulfate, aromatic hydroxydithiocarboxylic acids and their alkali metal salts, hydroquinone derivatives and catechol derivatives.

9. The rubber latex composition according to claim 1, wherein the vulcanization accelerator of the formula (1) is dibenzyldithiocarbamic acid, and the vulcanization accelerator of the formula (2) is zinc dibenzyldithiocarbamate.

10. The rubber latex composition according to claim 2, wherein the thiazole compound vulcanization accelerator is at least one compound selected from 2-mercaptobenzothiazole, dibenzothiazyl disulfide and a zinc salt of 2-mercaptobenzothiazole.

11. A rubber article dip-formed from the rubber latex composition as claimed in claim 1.

12. The dip-formed rubber article according to claim 11, which has an extracted nitrosamine content of not larger than 0.1 ppm.

13. The dip-formed rubber article according to claim 11, which is a medical article, a glove for home use or industrial use, a nipple or a balloon.

14. The dip-formed rubber article according to claim 13, wherein the medical article is a glove for operation, a glove for medical examination or detection, a balloon sac or a catheter.

* * * * *